US009651710B2

(12) United States Patent
Donzier et al.

(10) Patent No.: US 9,651,710 B2
(45) Date of Patent: May 16, 2017

(54) DOWNHOLE FLUID PROPERTIES ANALYSIS DEVICE AND TOOLS COMPRISING SUCH A DEVICE (71) Applicant: OPENFIELD, Versailles (FR)

(72) Inventors: Eric Donzier, Bercheres sur Vesgre (FR); Linda Abbassi, Montigny le Bretonneux (FR); Emmanuel Tavernier, Paris (FR)

(73) Assignee: OPENFIELD, Versailles (FR)

( * ) Notice: Subject to any disclaimer, the term of this patent is extended or adjusted under 35 U.S.C. 154(b) by 0 days.

(21) Appl. No.: 15/145,509

(22) Filed: May 3, 2016

(65) Prior Publication Data
US 2016/0327683 A1 Nov. 10, 2016

(30) Foreign Application Priority Data

May 4, 2015 (EP) .................................. 15166169

(51) Int. Cl.
G01V 8/20 (2006.01)
E21B 47/10 (2012.01)
E21B 49/08 (2006.01)
E21B 49/10 (2006.01)
G01V 8/02 (2006.01)
(Continued)

(52) U.S. Cl.
CPC .............. G01V 8/20 (2013.01); E21B 47/102 (2013.01); E21B 49/08 (2013.01); E21B 49/082 (2013.01); E21B 49/10 (2013.01); G01N 21/8507 (2013.01); G01N 33/2823 (2013.01); G01V 8/02 (2013.01); G01V 8/12 (2013.01);
(Continued)

(58) Field of Classification Search
CPC .......... E21B 49/10; E21B 49/082; G01V 8/20
See application file for complete search history.

(56) References Cited

U.S. PATENT DOCUMENTS 6,779,407 B2* 8/2004 Maute .................. E21B 47/011
73/861.12
2007/0068242 A1 3/2007 DiFoggio
(Continued)

FOREIGN PATENT DOCUMENTS

GB 2337106 A 11/1999

OTHER PUBLICATIONS

EP15166169 European Search Report, Oct. 6, 2015, European Patent Office, Munich, Germany.

Primary Examiner — Marcus Taningco
(74) Attorney, Agent, or Firm — The Jansson Firm; Pehr B. Jansson (57) ABSTRACT A downhole fluid properties analysis device connectable to a downhole sampling flow line having an internal diameter between 2 to 15 mm adapted to let flow the fluid, a hydrocarbon multiphase fluid from a hydrocarbon subsurface reservoir, to be analyzed. The analysis device includes an analysis pipe portion and a first optical probe arranged to transmit a light into the fluid and a second optical probe, connected to a spectrometer and arranged to produce a signal resulting from an interaction of the fluid with said light indicative of the downhole fluid properties. Each optical probe has an elongated body mounted through the wall of the analysis pipe portion and a needle-shaped tip with an external diameter less than 1 mm. The tips of the probes project into a flow section of the analysis pipe portion such that the first tip faces the second tip.

27 Claims, 6 Drawing Sheets (51) Int. Cl.
*G01V 8/12* (2006.01)
*G01N 21/85* (2006.01)
*G01N 33/28* (2006.01)
*G01N 21/31* (2006.01)
*G01N 21/68* (2006.01)

(52) U.S. Cl.
CPC .............. *G01N 21/31* (2013.01); *G01N 21/68* (2013.01); *G01N 2201/06113* (2013.01)

(56) References Cited

U.S. PATENT DOCUMENTS

| | | | |
|---|---|---|---|
| 2008/0307860 A1* | 12/2008 | Guieze | G01F 1/7086 73/61.44 |
| 2009/0158837 A1* | 6/2009 | Meek | E21B 17/10 73/152.24 |
| 2011/0083842 A1* | 4/2011 | Indo | E21B 49/10 166/250.01 |
| 2012/0175510 A1* | 7/2012 | Zhou | G01N 33/2823 250/255 |
| 2014/0353481 A1* | 12/2014 | Daito | G01V 8/10 250/269.1 |
| 2014/0361155 A1 | 12/2014 | Daito | |
| 2016/0178435 A1* | 6/2016 | Indo | E21B 49/10 356/326 |
| 2016/0178793 A1* | 6/2016 | Vijayakumar | G01N 33/2841 356/409 |

* cited by examiner

DOWNHOLE FLUID PROPERTIES ANALYSIS DEVICE AND TOOLS COMPRISING SUCH A DEVICE

TECHNICAL FIELD

The invention relates to a downhole fluid properties analysis device and a downhole fluid analysis tool comprising such a fluid properties analysis device. The invention is particularly applicable to the analysis of a multiphase fluid mixture flowing from a hydrocarbon bearing zone into a hydrocarbon well by means of a formation tester tool that operates at downhole pressure and temperature conditions. The invention applies to the analysis of the optical properties of such fluid flowing in downhole sampling flow lines of small dimension (millimeters range) of the formation tester tool. The invention is particularly applicable to the characterization in real time of hydrocarbon reservoir fluids (e.g. crude oil, gas, brines).

BACKGROUND

The documents U.S. Pat. No. 4,994,671, US2014/0361155 and the Technical Paper "Advanced Downhole Fluid Analysis" IBP3075_10 of Rio Oil & Gas Expo and Conference 2010 held 13-16 Sep. 2010 in Rio de Janeiro presented by Brazilian Petroleum, Gas and Biofuels Institute—IBP, Jesus A. Canas et al. describe Downhole Fluid Analysis (DFA) using a wireline formation tester tool, in particular a modular formation dynamics tester tool. A formation tester tool is used to take samples of reservoir fluids directly from hydrocarbon bearing zone. A formation tester tool that includes a DFA tool is used to measure physical and chemical properties of reservoir fluids during the sampling phase of the formation tester tool. The DFA tool enables having access to real time information on fluids during the sampling phase.

Figure 1:
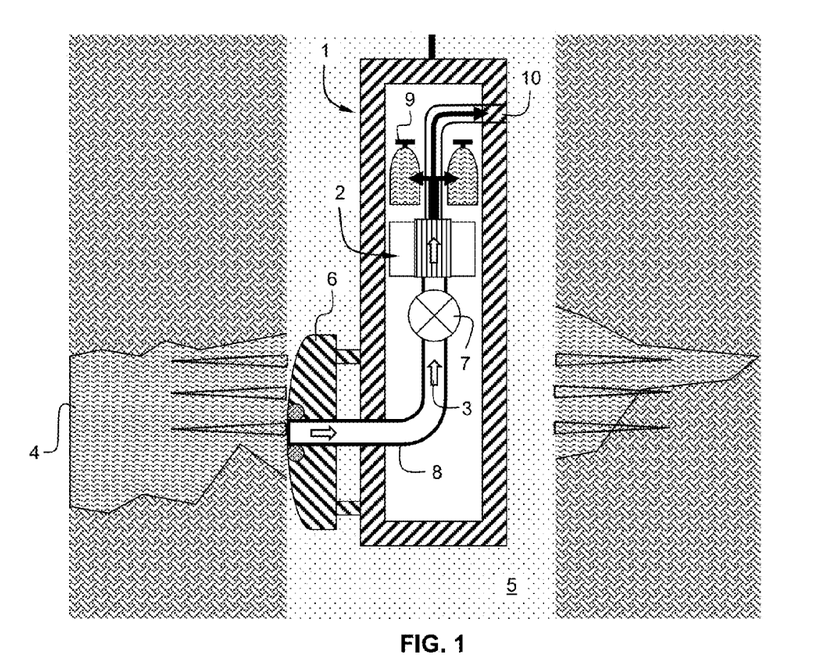
FIG. 1 is a cross-section view schematically illustrating a formation tester tool including a downhole fluid analysis tool sampling a fluid flowing from a subsurface reservoir zone.

FIG. 1 is a cross-section view schematically illustrating a formation tester tool 1 including a DFA tool 2 sampling a reservoir fluid 3 flowing from a hydrocarbon bearing zone 4 into a hydrocarbon well 5 that has been drilled into an earth formation. Generally, the formation tester tools and DFA tools have a cylindrical shape that is adapted to travel into well bore hole. The formation tester tool 1 is suspended in the borehole of the well from a lower end of a logging cable or wireline spooled on a winch at the surface (not shown). The logging cable is coupled to a surface electrical control system having appropriate electronics and processing systems (not shown). The fluid 3 enters the formation tester tool 1 at a formation pad 6 applied to the wall of the well 5 in a sealed manner. The fluid 3 is pumped by means of a pump 7 though a downhole sampling flow line 8 extending internally of the formation tester tool 1. The fluid 3 is directed towards the downhole fluid analysis tool 2 for real time analysis and also towards a tool module storing samples in bottles for delayed analysis in surface laboratories. The remaining fluid 3 can also be discarded out of the formation tester tool 1 by an outlet 10 into the well 5.

The formation tester and the DFA tools operate in harsh environment, namely extreme conditions including high pressure from several hundred bars up to 2000 bars, high temperature up to 200° C., presence of corrosive fluids such as sulfuric acid, presence and contamination by solid particles such as scales, asphaltenes, sand particles, as well as multiphasic flow conditions (oil, gas, water). Further, there are also the space and power constraints associated to downhole tools deployment. Furthermore, there is the high shocks environment associated to wireline or drilling operations.

Figure 2:
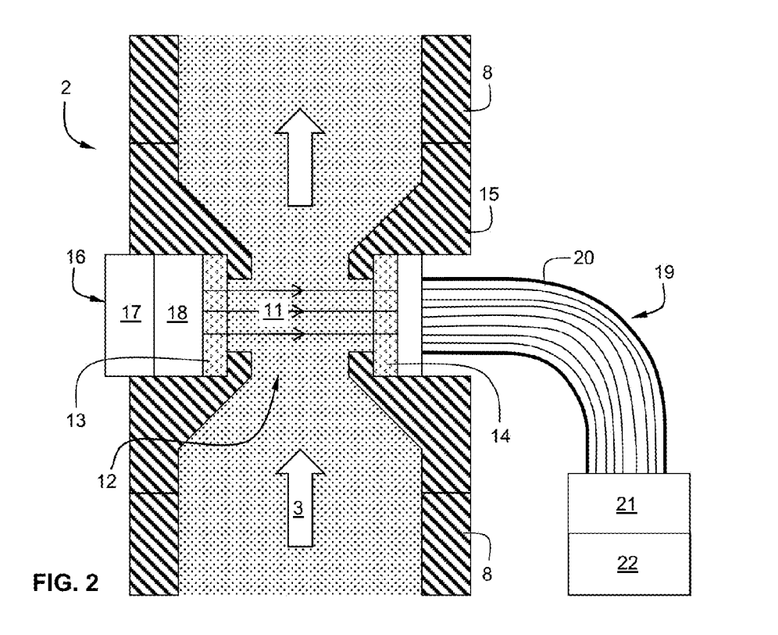
FIG. 2 is a detailed cross-section view schematically illustrating a downhole fluid analysis cell of the downhole fluid analysis tool of FIG. 1 according to the prior art.

FIG. 2 is a detailed cross-section view schematically illustrating a DFA cell of the DFA tool of FIG. 1. The evaluation of fluid properties by the DFA tool 2 is based on the transmission of light 11 through the fluid sample and the measurement of the attenuation at different wavelengths. Optical absorption spectra are obtained that can be related to critical fluid characteristics such as for example Gas Oil Ratio, $CO_2$ and other relative concentrations of chemical compounds. A state of the art DFA cell 12 for optical transmission measurements comprises sapphire windows 13, 14 assembled to metal body parts 15 made of high strength corrosion resistant alloys such as Inconel. The metal body parts 15 forms a fluid flow restriction. The emission module 16 comprises a light source 17 and filters 18. The reception module 19 comprises an optical fiber bundles collecting light to filters 21 and photo detectors 22 of a spectrometer. More recently continuous absorption spectra in the near infrared region have been developed based on gratings spectrometers specially engineered in order to withstand harsh conditions.

The drawbacks of such conventional sapphire windows approach are the following:

Low performance of compositional analysis—The optical path length selection (light travel distance inside the fluid) is constrained by the fluid flow restriction that can be accepted without altering the sampling process and/or the representativeness of the fluid sample present in between the two windows. Distance between windows below 1 mm is in practice impossible to implement and typical optical path lengths for current commercial tools are within the 3-5 mm range. This limitation has forced engineers to favor analysis in the visible-near infrared spectrum where attenuation factors in hydrocarbon fluids are relatively low, despite the fact that absorption peaks are related to overtones of the vibration modes of the molecules to be detected and suffer from peak enlargements and overlaps from different compounds. This leads to complex interpretation and relatively poor robustness and performance of compositional analysis.

Optical cell contamination—Relatively large optical window surface (several $mm^2$) and even more importantly its large curvature ratio (superior to 1 mm) favor the formation of droplets of fluids sticking on the window surface and altering analysis.

Complex and expensive hardware—The window assembly (the conventional method is sapphire disk or tube brazing onto metal) is critical in order to withstand high pressure and high temperature.

Optical path—The optical path length is fixed and can only be changed at the manufacturing step of the cell.

Cleaning—The complex mechanical configuration of the cell flow line and windows leads to dead volumes which make the cleaning of the cell flow line during the early phase of the sampling a critical step.

SUMMARY OF THE DISCLOSURE

It is an object of the invention to propose a fluid optical properties analysis device that overcome one or more of the limitations of the existing methods and/or devices.

According to one aspect, there is provided a downhole fluid properties analysis device connectable to a downhole sampling flow line, the downhole sampling flow line having an internal diameter between 2 to 15 mm adapted to let flow the fluid to be analyzed, the fluid being a hydrocarbon multiphase fluid mixture from a hydrocarbon subsurface reservoir, the downhole fluid properties analysis device comprising:

an analysis pipe portion;

a first optical probe and a second optical probe, the first optical probe being a light emitting probe adapted to be coupled to a light source and arranged to transmit a light into the fluid, and the second optical probe being a light receiving probe adapted to be connected to a spectrometer and arranged to produce a signal resulting from an interaction of the fluid with said light indicative of the downhole fluid properties; wherein:

each of said optical probes comprises an elongated body mounted through the wall of the analysis pipe portion in a sealed manner and having a tip, the tip being needle shaped and having an external diameter less than 1 mm; and the first tip of the first optical probe and the second tip of the second optical probe project into a flow section of the analysis pipe portion such that the first tip faces the second tip at a defined distance ranging from 10 µm to 99 mm.

The analysis pipe portion may comprise a first and a second hole facing each other, a portion of each elongated body being inserted into the analysis pipe portion through the first and second hole respectively, and wherein the device comprises at least one probe connector to couple at least one optical probe in sealed manner to one of the hole, and adapted to adjust the position of said optical probe relatively to the hole of the analysis pipe portion so as to control the defined distance between both tips.

The optical probes may be directed transversally relatively to a longitudinal axis of the analysis pipe portion.

The optical probes may be parallel to a longitudinal axis of the analysis pipe portion.

The axis of the analysis pipe portion may be parallel to an axis of the downhole sampling flow line.

The probe connector may be chosen among the group comprising a screw nut connection including a conical synthetic rubber/fluoropolymer elastomer ferrule, or a screw nut connection including a metal ferrule, or a screw nut connection including an O-ring, or a welded connection.

The optical probe may comprise an optical element under the form of an optical fiber and a sapphire tip located in the central portion of the elongated body under the form of a protective tube, an end portion of said optical element forming a tip end adapted to be in contact with the fluid to be analyzed.

The optical probe may further comprise an electronic board coupled to the optical element and integrating a measurement circuit and a processing module so as to deliver digital measurements on an output cable.

The analysis pipe portion may further comprise a third hole receiving a third optical probe in sealed manner, the third optical probe being positioned perpendicularly relatively to an optical transmission path defined between the first and second optical probe.

According to a further aspect, there is provided a downhole fluid analysis tool comprising a sampling device having a downhole sampling flow line connected to at least one downhole fluid properties analysis device of the invention.

According to still a further aspect, there is provided a formation tester tool adapted for displacement along and within a bore hole of a hydrocarbon well, comprising a sampling device having a downhole sampling flow line connected to at least one downhole fluid properties analysis device of the invention.

With the invention, it is possible to achieve optical path lengths in a flexible manner from a few tens of microns to several tens millimeters.

The fluid optical properties analysis device of the invention is used for real time in line fluid analysis in downhole sampling system for oil and gas reservoirs evaluation, downhole hydrocarbon fluids characterization, and produced fluids compositional analysis in hydrocarbon wells.

Other advantages will become apparent from the hereinafter description of the invention.

BRIEF DESCRIPTION OF THE DRAWINGS

The present invention is illustrated by way of examples and not limited to the accompanying drawings, in which like references indicate similar elements.

DETAILED DESCRIPTION

The invention will be understood from the following description, in which reference is made to the accompanying drawings.

Figure 3:
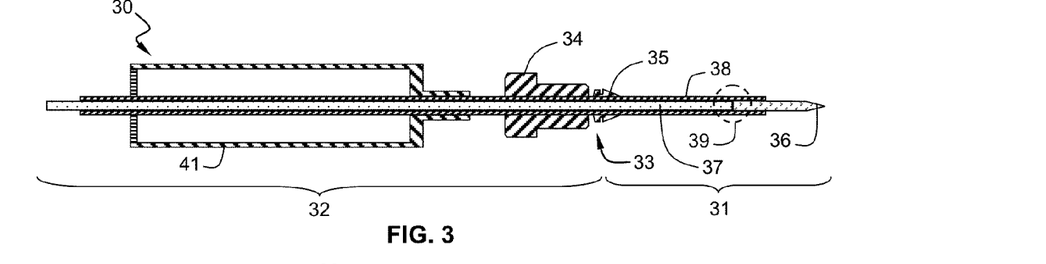
FIGS. 3, 4 and 5 are cross section and perspective views showing an embodiment of an optical probe according to the invention.
Figure 4:
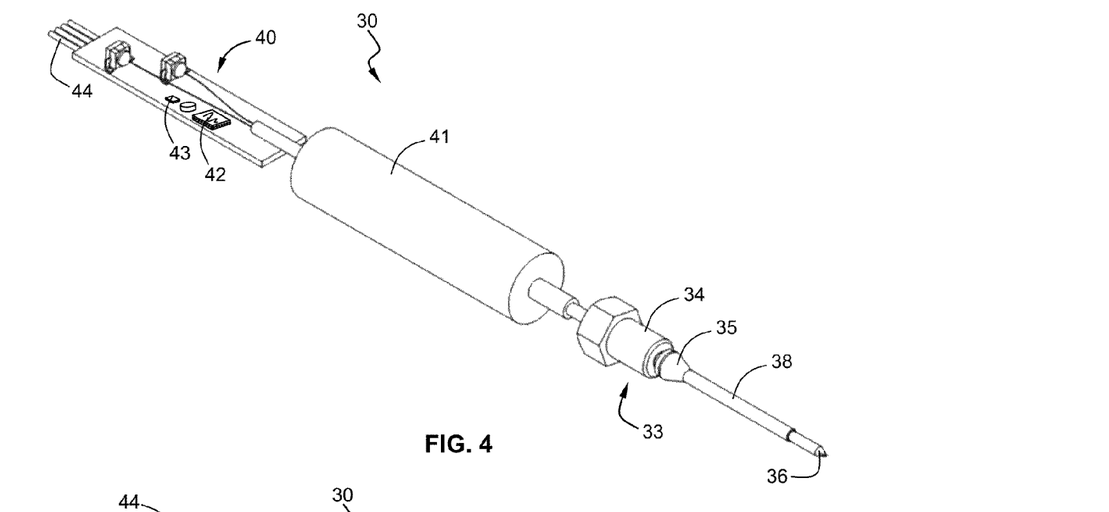
Figure 5:
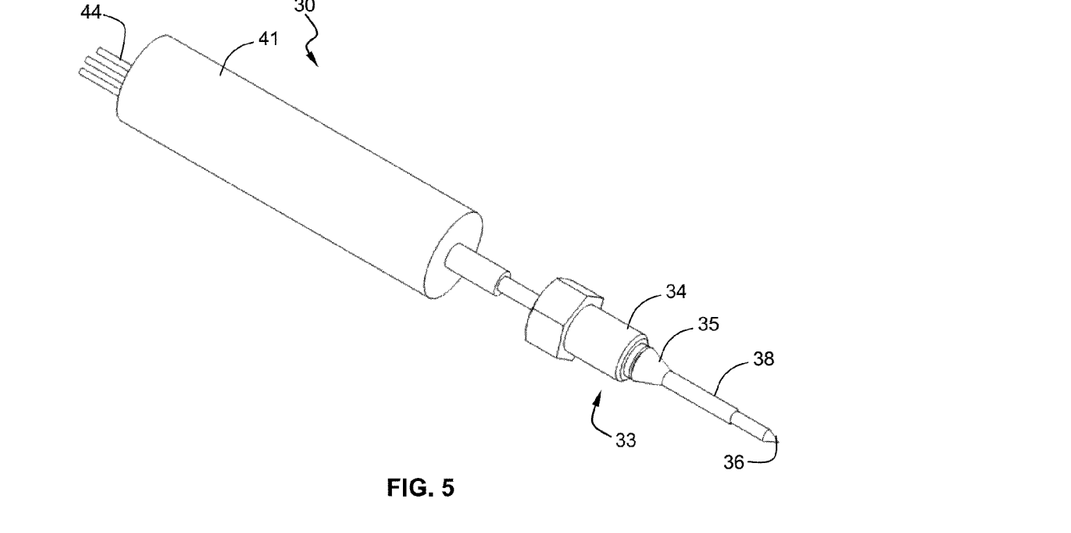

FIG. 3 is a cross section view showing an embodiment of an optical probe 30. FIG. 4 is a perspective view showing the optical probe 30 in a configuration where the electronic board 40 is out of the protective housing 41. FIG. 5 is a perspective view showing the optical probe 30 in a configuration reading to be connected to an analysis cell.

The optical probe 30 has the general shape of an elongated cylindrical body having a first portion 31 in contact with the well fluid to be analyzed (i.e. in contact with harsh environments), and a second portion 32 separated from the fluid to be analyzed (protected from harsh environments). A probe connector 33 separates the first portion 31 from the second portion 32. The first portion 31 comprises an optical tip 36 coupled to at least one optical fiber 37 (e.g. silica fiber), a protective tube 38 surrounding the optical fiber 37, a coupling zone 39 between the optical tip 36 and the optical fiber 37. The protective tube 38 partially surrounds the optical tip 36 at the coupling zone 39, letting the distal part of the optical tip 36 in contact with the fluid to be measured. The second portion 32 comprises an electronic board 40 coupled to the optical fiber 37, and a protective housing 41. FIG. 4 shows an embodiment comprising two optical fibers 37. The electronic board 40 may integrate an optoelectronics module comprising a measurement circuit 42 and a processing module 43 achieving light amplitude and/or spectral analysis so as to deliver digital measurements on output cables 44.

The optical tip 36 is a sapphire rod having a needle shape. The external diameter of the sapphire rod ranges from about 0.3 mm to about 1 mm. The sapphire material has a particular robustness in corrosive environments. The needle shape has the property of self cleaning in multiphasic conditions. At least droplets of fluids rarely stick on such a tip.

The protective tube 38 is made of metal or alloy. Metal or alloy offering high strength and high chemical resistance such as Inconel can suitably be used. The protective tube 38 is used to mechanically maintain the sapphire rod optical tip 36 ensuring a pressure tight connection to the optical fiber 37, to protect the optical fiber 37 from fluids and to hold the probe connector 33. The protective tube 38 is sealed against the optical tip 36 in order to avoid penetration of fluid towards the optical fiber 37 and the second portion 32. As a particular example, the protective tube 38 has an external diameter of 0.5 mm to 3 mm, and is a few centimeters long (e.g. 25.4 cm/10 inches).

In an exemplary embodiment, the probe connector 33 may slide onto the protective tube 38 and is sealed against the protective tube 38 once in place. The probe connector 33 is adapted to be connected by a screw nut type connection to a hole of the analysis pipe portion as depicted in FIGS. 6-11. The probe connector 33 enables adjusting the position of the optical probe relatively to the hole of the analysis pipe portion so as to control the distance between the tips 36 of two vis-à-vis probes. The screw nut connection may be a conical synthetic rubber/fluoropolymer elastomer ferule 35 (metal-elastomer seal), or a conical metal ferrules 35 (metal-metal seal). For example, synthetic rubber/fluoropolymer elastomer may be Viton fluoroelastomers a registered trademark of DuPont Performance Elastomers L.L.C. A high pressure seal connection is obtained when the screw 34 associated with the conical ferule 35 both slidingly coupled to the protective tube 38 is appropriately screwed into a threaded hole. Other waterproof and high pressure connections may be appropriate, for example a screw nut connection including an O-ring. As a further alternative the connection may be a welded connection, meaning that once the distance has been set at manufacturing step, the protective tube 38 is welded to a hole in the analysis pipe portion.

Figure 6:
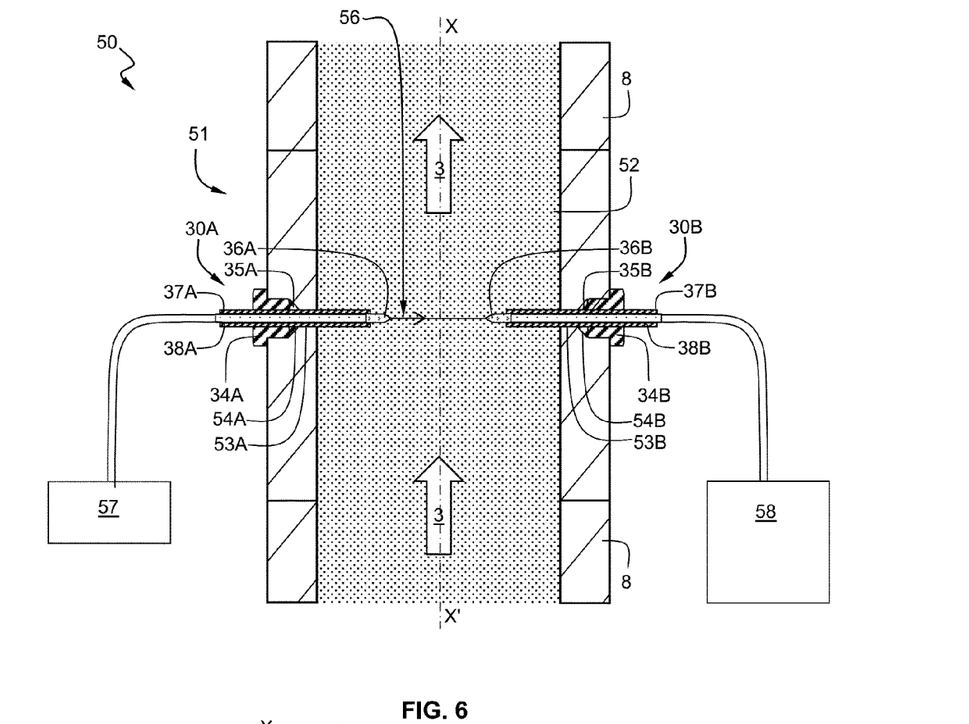
FIGS. 6 and 7A are cross section and perspective exploded views showing a first embodiment of a downhole fluid analysis cell according to the invention.
Figure 7A:
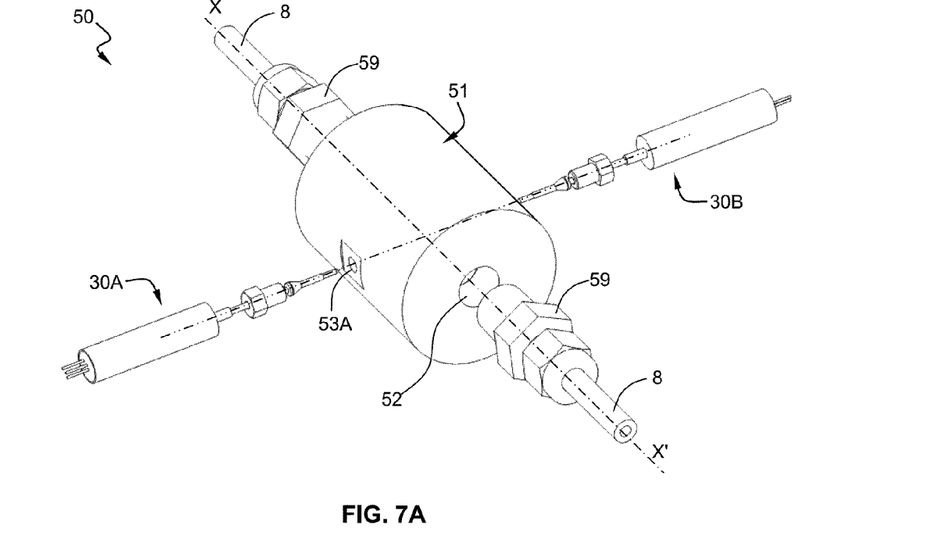

FIGS. 6 and 7A are cross section and perspective exploded views showing a first embodiment of a downhole fluid analysis tool 50 comprising a downhole fluid analysis cell 51. The downhole fluid analysis cell 51 is connected to the downhole sampling flow line 8 by means of appropriate connectors 59. The downhole fluid analysis cell 51 comprises an analysis pipe portion 52, and first and second threaded holes 53A, 53B. The analysis pipe portion 52 is a cylindrical cavity extending along a longitudinal axis XX' of the downhole fluid analysis cell 51 and having dimension similar to the downhole sampling flow line 8. The longitudinal axis XX' substantially corresponds to the fluid flow 3 direction in the downhole sampling flow line 8. The first and second threaded hole 53A, 53B faces each other positioned transversally relatively to the longitudinal axis XX' of the downhole fluid analysis cell 51. A first optical sonde 30A is inserted into the first threaded hole 53A and tightly connected by means of the probe connector, the ferule 35A being deformed by the screw 34A against a conical shoulder 54A of the first threaded hole 55A. Similarly, a second optical sonde 30B is inserted into the second threaded hole 53B and tightly connected by means of the probe connector, the ferule 35B being deformed by the screw 34B against a conical shoulder 54B of the second threaded hole 55B. The optical tips 36A, 36B respectively face each other inside the downhole fluid analysis cell 51 where the fluid 3 is flowing. One of the optical probe, for example the first optical probe 30A is used as light emitting probe by being connected to a light source 57. The other optical probe, for example the second optical probe 30B is used as a light receiving probe by being connected to a spectrometer 58. An optical transmission path 56 is created between both optical tips 36A, 36B. The spectrometer 58 computes absorption spectrum of the fluid which is then converted into compounds concentration using appropriate models and calibrations data. As an example, the first tip 36A of the first probe 30, 30A faces the second tip 36B of the second probe 30B at a defined distance ranging from 10 µm to 99 mm.

Figure 7B:
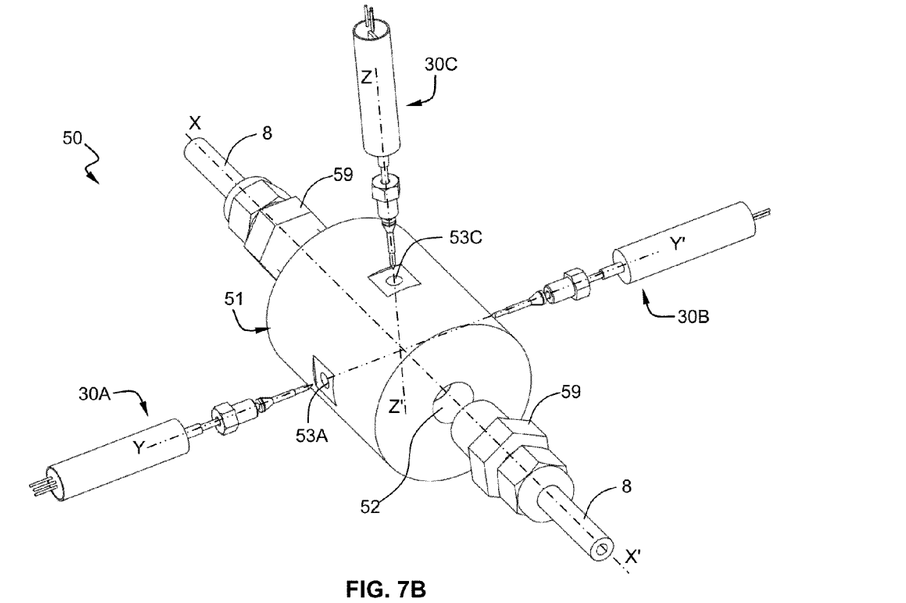
FIG. 7B is a perspective exploded view showing an alternative to the first embodiment of a downhole fluid analysis cell according to the invention.
Figure 8:
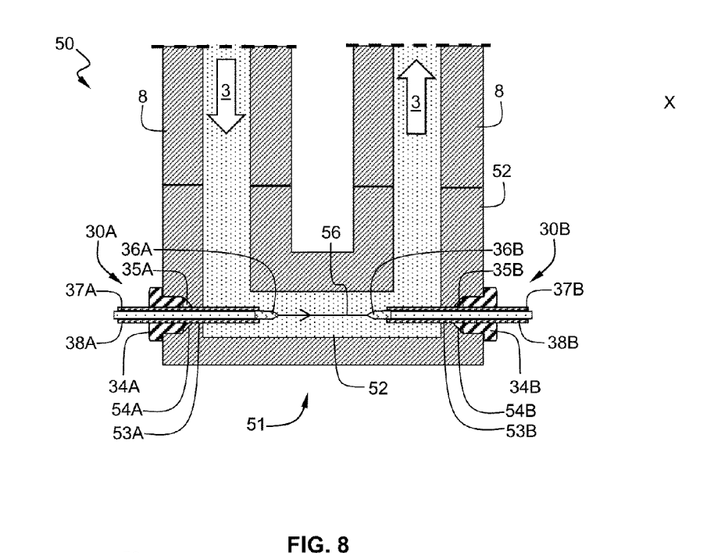
FIGS. 8, 9, 10 and 11 are cross section, bottom and perspective views showing a second embodiment of a downhole fluid analysis cell according to the invention.

FIG. 7B is a perspective exploded view showing an alternative to the first embodiment of the downhole fluid analysis tool 50 comprising the downhole fluid analysis cell 51. According to this alternative embodiment, the downhole fluid analysis cell 51 comprises an analysis pipe portion 52, and first, second and third threaded holes 53A, 53B, 53C. As in the first embodiment, the first and second threaded hole 53A, 53B faces each other positioned transversally according to transversal axis YY' relatively to the longitudinal axis XX' of the downhole fluid analysis cell 51. Differing from the first embodiment, the third threaded hole 53C is positioned transversally according to transversal axis ZZ' relatively to the longitudinal axis XX' of the downhole fluid analysis cell 51 and to the transversal axis YY' defined by the first and second optical sonde 30A, 30B. The first optical sonde 30A is inserted into the first threaded hole 53A. The second optical sonde 30B is inserted into the second threaded hole 53B. Similarly, a third optical sonde 30C is inserted into the third threaded hole 53C. The three optical sonde 30A, 30B and 30C are tightly connected by means of the probe connector. The third optical sonde 30C positioned perpendicularly relatively to the optical transmission path 56 is used to detect scattered light. The measurement of scattered light enables detecting small droplets, bubbles or solid particles in liquids. Thus, in this first configuration of the downhole fluid analysis tool 50, the third optical sonde 30C is adapted for the measurement of water turbidity. In a second configuration, the third optical sonde 30C positioned perpendicularly relatively to the optical transmission path 56 is used to illuminate the fluid with a light of high energy (e.g. the third optical sonde 30C is coupled to a laser source). The molecules present in the fluid are locally excited and re-emits in a light spectra comprising various light rays related to the chemical compounds present in the fluid. The positioning of the third optical sonde 30C coupled to the laser source substantially perpendicularly to the optical transmission path 56 defined by the two other probes enables avoiding blinding the optical sonde used as a detector with direct high energy light.

With the optical probe of the invention, it is possible to adjust the position of the first optical probe 30A, or of the second optical probes 30B, or of both probes 30A, 30B respectively relatively to the threaded holes 53A, 53B respectively so as to control the length of the optical path 56 between both tips. This length adjustment is easy to perform by sliding probes inside the analysis pipe portion 52 without requiring restriction on the analysis pipe portion itself. The tip of the optical probe provides minimal intrusion into the analysis pipe portion and minimal limitation effect onto the fluid flow. Also, the mechanical position of both tips is rigidly defined and a high pressure leak proof barrier is obtained by means of the probe connector.

With the invention, it is possible to adjust the optical path length from a few tens of microns to several centimeters such as to adapt the spectroscopy to the type of fluid to be analyzed (from light to dark crude oils, gas condensates, dry gas, etc . . . ). In particular, it enables spectroscopy in the mid Infrared region. This represents a drastic improvement of fluid compositional analysis accuracy and robustness over state of the art optical measurement with DFA using windows (e.g. sapphire windows).

The adjustment of the position of the probes, i.e. optical path 56 length can be made small or large without constraining the flow line configuration or operation. This adjustment is made at the manufacturing of the downhole fluid properties analysis device 51. Alternatively, the optical path 56 length can be changed at a later time, in particular during the maintenance of the tool, or virtually at any time in case the probe connector is coupled to a motorized screwing mechanism (not shown).

FIGS. 8, 9, 10 and 11 are cross section, bottom and perspective views showing a second embodiment of a downhole fluid analysis tool 50 comprising a downhole fluid analysis cell 51. The second embodiment mainly differs from the first embodiment in that the optical probes 30A and 30B are parallel to the analysis pipe portion 52, in other word according to the longitudinal axis XX' corresponding to the fluid flow 3 direction in the downhole sampling flow line 8. The light source and spectrometer are omitted in these FIGS.

The second embodiment enables having the optical probes inserted along the length of the downhole fluid analysis cell 51. This configuration allows a wider optical path length control and is also more adapted to packaging inside a tube shaped tool like a formation tester tool.

The distance between the tips 36A and 36B of the optical probes in order to define the optical path length 56 is selected according to attenuation factors to be measured. The attenuation factor may range from several orders of magnitude which require an optical path length from a few tens of microns to a few tens of millimeters depending on fluid composition and light wavelengths. The invention enables a fine definition of the optical path length 56 by sliding the optical probe into the threaded holes 53A, 53B as hereinbefore described.

Figure 9:
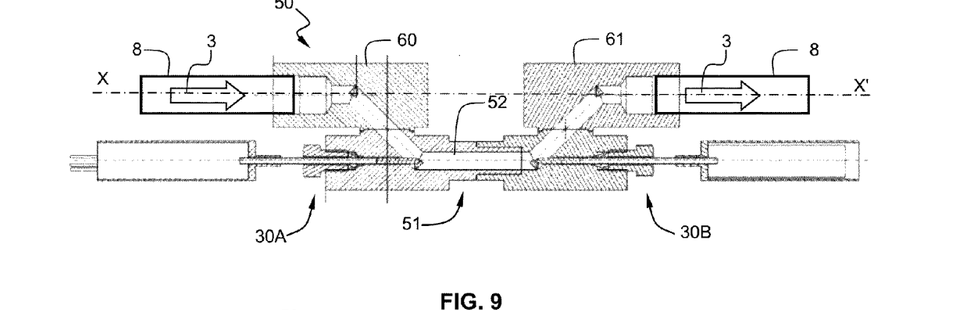
Figure 10:
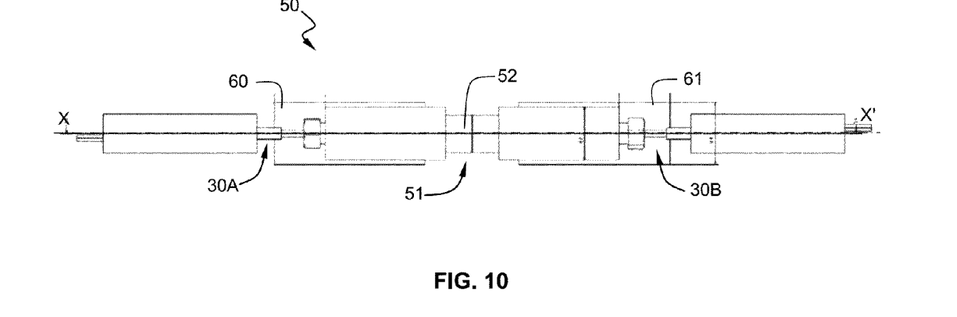
Figure 11:
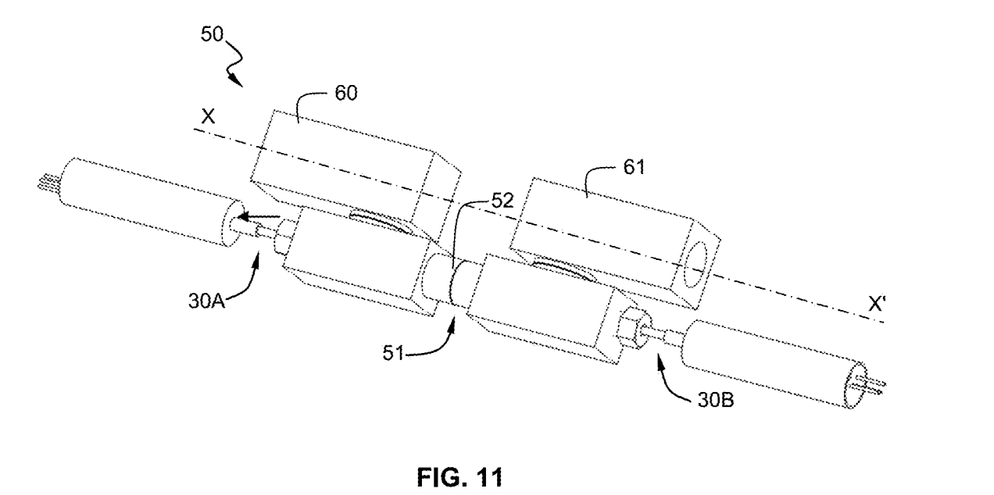

FIGS. 9-11 illustrate a particular implementation of the downhole fluid analysis cell 51 that is particularly well adapted for integration in a wireline formation tester tool as shown in FIG. 1. The downhole fluid analysis cell 51 comprises an inlet fluid connector 60 and an outlet fluid connector 61 positioned above and coupled upstream, respectively downstream to the downhole fluid analysis cell 51. This enables space saving by superposing the optical probe with the downhole sampling flow line 8.

Figure 14:
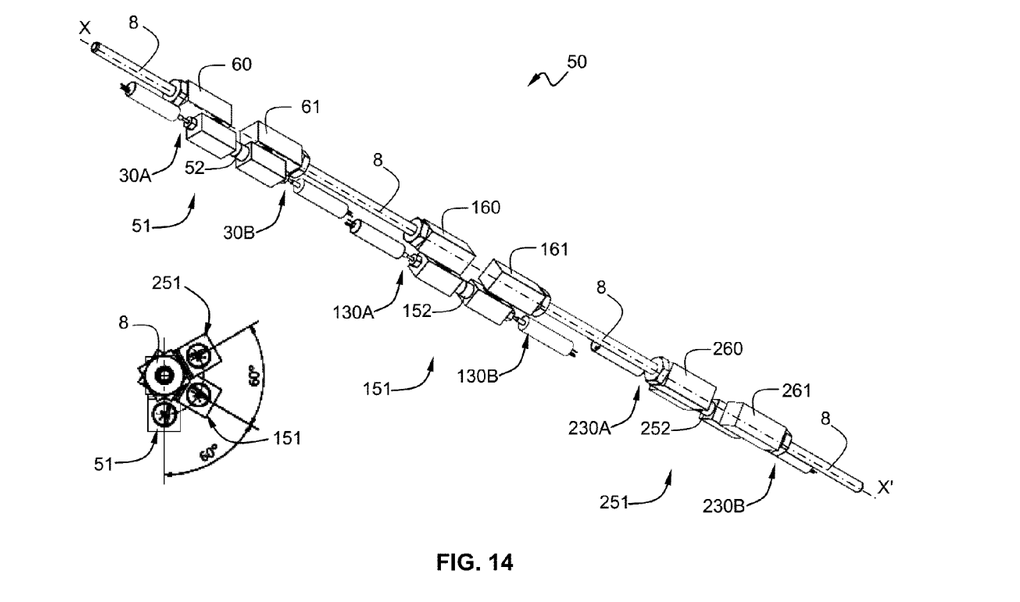
FIG. 14 shows side and perspective views illustrating a train of downhole fluid analysis cells according to the invention.

FIG. 14 shows side and perspective views illustrating a downhole fluid analysis tool 50 in the form of a train of three downhole fluid analysis cells 51, 151 and 251 assembled along the downhole sampling flow line 8. Each downhole fluid analysis cell 51, 151 and 251 comprises an inlet fluid connector 60, 160 and 260 and an outlet fluid connector 61, 161 and 261 positioned above and coupled upstream, respectively downstream to the downhole fluid analysis cell 51, 151 and 251 respectively. Each downhole fluid analysis cell 51, 151 and 251 comprises the probes 30A/30B, 130A/130B, 230A/230B that are directed in line with the analysis pipe portion 52, 152 and 252, respectively. Each downhole fluid analysis cell 51, 151 and 251 is rotated relatively to the other from an angle of 60°. This enables a very compact implementation of a train of downhole fluid analysis cells 51, 151 and 251 along the downhole sampling flow line 8 (see in particular the side view).

Figure 12:
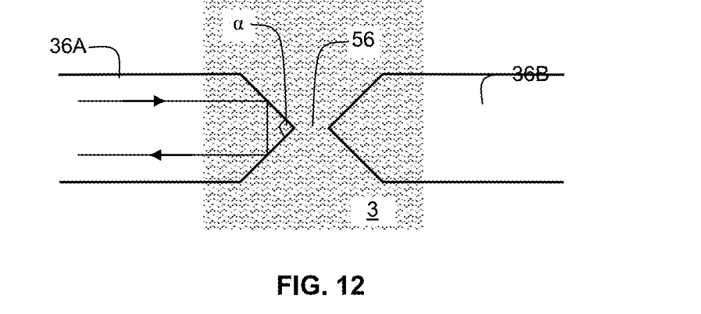
FIGS. 12 and 13 illustrate the optical measurement principle with two optical probes.
Figure 13:
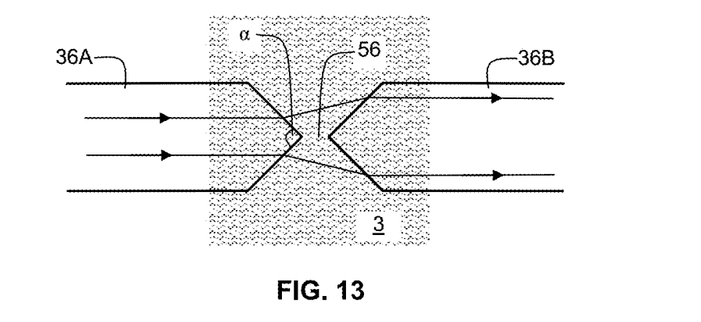

FIGS. 12 and 13 illustrate the optical measurement principle with two optical probes.

In an embodiment of the optical probe the sapphire tip 36A, 36B has a conical shape with a tip angle $\alpha$ of 90°. In the presence of gas (FIG. 12), there is a total reflection at the light emitting probe tip 36A, there is no light received at the light receiving probe tip 36B. In the presence of oil (FIG. 13), light is transmitted from the light emitting probe tip 36A towards the light receiving probe tip 36B (i.e. Transmission measurements). Therefore, such a tip enables discriminating gas from liquid. Further, the sharp end of the sapphire tip 36A, 36B promotes fluid droplets removal from the optical path 56.

The fluid optical properties analysis tool of the invention has the following advantages over the windows based DFA tool:

There is no flow restriction even with small optical path lengths, thus enabling measurements even in highly attenuative fluids;

There is no dead volume incumbent to the analysis cell assembly, thus cancelling at least greatly reducing analysis pipe contamination;

The self cleaning in multiphasic environments is fast, eliminating or at least greatly reducing probes contamination;

The optical path lengths is adjustable; and

The integration of new probes in the DFA tool is easy.

The drawings and their description hereinbefore illustrate rather than limit the invention.

It should be appreciated that embodiments of the present invention are not limited to embodiments showing a vertical well bore, said embodiments may also apply to a horizontal or deviated well bore. In the frame of oilfield industry, all the embodiments of the present invention are equally applicable to cased and uncased borehole (open hole), and also other kind of conduits or device where a fluid may flow. Furthermore, also two embodiments have been shown wherein the probes are directed transversally or parallel relatively to a longitudinal axis of the analysis pipe portion, the probes may also be positioned at angle relatively to a longitudinal axis of the analysis pipe portion (e.g. 30°, 45°, etc . . . ) provided that the probe are directed towards the same axis.

The invention claimed is:

1. A downhole fluid properties analysis device connectable to a downhole sampling flow line, the downhole sampling flow line having an internal diameter between 2 to 15 mm adapted to let flow the fluid to be analyzed, the fluid being a hydrocarbon multiphase fluid mixture from a hydrocarbon subsurface reservoir, the downhole fluid properties analysis device comprising:

an analysis pipe portion;

a first optical probe and a second optical probe, the first optical probe being a light emitting probe adapted to be coupled to a light source and arranged to transmit a light into the fluid, and the second optical probe being a light receiving probe adapted to be connected to a spectrometer and arranged to produce a signal resulting from an interaction of the fluid with said light indicative of the downhole fluid properties;

wherein:
each of said optical probes comprises an elongated body mounted through the wall of the analysis pipe portion in a sealed manner and has a tip, the tip being needle shaped and having an external diameter less than 1 mm; and the first tip of the first optical probe and the second tip of the second optical probe project into a flow section of the analysis pipe portion such that the first tip faces the second tip at a defined distance ranging from 10 µm to 99 mm.

2. The device of claim 1, wherein the analysis pipe portion comprises a first and a second hole facing each other, a portion of each elongated body being inserted into the analysis pipe portion through the first and second hole respectively, and wherein the device comprises at least one probe connector to couple at least one optical probe in sealed manner to one of the hole, and adapted to adjust the position of said optical probe relatively to the hole of the analysis pipe portion so as to control the defined distance between both tips.

3. The device of claim 1, wherein the optical probes are directed transversally relatively to a longitudinal axis of the analysis pipe portion.

4. The device of claim 1, wherein the optical probes are parallel to a longitudinal axis of the analysis pipe portion.

5. The device according to claim 1, wherein the axis of the analysis pipe portion is parallel to an axis of the downhole sampling flow line.

6. The device according to claim 2, wherein the probe connector is chosen among the group comprising a screw nut connection including a conical synthetic rubber/fluoropolymer elastomer ferrule, or a screw nut connection including a metal ferrule, or a screw nut connection including an O-ring, or a welded connection.

7. The device according to claim 2, wherein the analysis pipe portion further comprises a third hole receiving a third optical probe in sealed manner, the third optical probe being positioned perpendicularly relatively to an optical transmission path defined between the first and second optical probe.

8. The device according to claim 1, wherein the optical probe comprises an optical element under the form of an optical fiber and a sapphire tip located in the central portion of the elongated body under the form of a protective tube, an end portion of said optical element forming a tip end adapted to be in contact with the fluid to be analyzed.

9. The device of claim 8, wherein the optical probe further comprises an electronic board coupled to the optical element and integrating a measurement circuit and a processing module so as to deliver digital measurements on an output cable.

10. A downhole fluid analysis tool comprising a sampling device having a downhole sampling flow line connected to at least one downhole fluid properties analysis device, the downhole sampling flow line having an internal diameter between 2 to 15 mm adapted to let flow the fluid to be analyzed, the fluid being a hydrocarbon multiphase fluid mixture from a hydrocarbon subsurface reservoir, the downhole fluid properties analysis device comprising:
an analysis pipe portion;
a first optical probe and a second optical probe, the first optical probe being a light emitting probe adapted to be coupled to a light source and arranged to transmit a light into the fluid, and the second optical probe being a light receiving probe adapted to be connected to a spectrometer and arranged to produce a signal resulting from an interaction of the fluid with said light indicative of the downhole fluid properties;
wherein:
each of said optical probes comprises an elongated body mounted through the wall of the analysis pipe portion in a sealed manner and has a tip, the tip being needle shaped and having an external diameter less than 1 mm; and the first tip of the first optical probe and the second tip of the second optical probe project into a flow section of the analysis pipe portion such that the first tip faces the second tip at a defined distance ranging from 10 µm to 99 mm.

11. The downhole fluid analysis tool of claim 10, wherein the analysis pipe portion comprises a first and a second hole facing each other, a portion of each elongated body being inserted into the analysis pipe portion through the first and second hole respectively, and wherein the device comprises at least one probe connector to couple at least one optical probe in sealed manner to one of the hole, and adapted to adjust the position of said optical probe relatively to the hole of the analysis pipe portion so as to control the defined distance between both tips.

12. The downhole fluid analysis tool of claim 10, wherein the optical probes are directed transversally relatively to a longitudinal axis of the analysis pipe portion.

13. The downhole fluid analysis tool of claim 10, wherein the optical probes are parallel to a longitudinal axis of the analysis pipe portion.

14. The downhole fluid analysis tool of claim 10, wherein the axis of the analysis pipe portion is parallel to an axis of the downhole sampling flow line.

15. The downhole fluid analysis tool of claim 11, wherein the probe connector is chosen among the group comprising a screw nut connection including a conical synthetic rubber/fluoropolymer elastomer ferrule, or a screw nut connection including a metal ferrule, or a screw nut connection including an O-ring, or a welded connection.

16. The downhole fluid analysis tool of claim 11, wherein the analysis pipe portion further comprises a third hole receiving a third optical probe in sealed manner, the third optical probe being positioned perpendicularly relatively to an optical transmission path defined between the first and second optical probe.

17. The downhole fluid analysis tool of claim 10, wherein the optical probe comprises an optical element under the form of an optical fiber and a sapphire tip located in the central portion of the elongated body under the form of a protective tube, an end portion of said optical element forming a tip end adapted to be in contact with the fluid to be analyzed.

18. The downhole fluid analysis tool of claim 17, wherein the optical probe further comprises an electronic board coupled to the optical element and integrating a measurement circuit and a processing module so as to deliver digital measurements on an output cable.

19. A formation tester tool (1) adapted for displacement along and within a bore hole (5) of a hydrocarbon well, comprising a sampling device having a downhole sampling flow line (8) connected to at least one downhole fluid properties analysis device, the downhole sampling flow line having an internal diameter between 2 to 15 mm adapted to let flow the fluid to be analyzed, the fluid being a hydrocarbon multiphase fluid mixture from a hydrocarbon subsurface reservoir, the downhole fluid properties analysis device comprising:
an analysis pipe portion;
a first optical probe and a second optical probe, the first optical probe being a light emitting probe adapted to be coupled to a light source and arranged to transmit a light into the fluid, and the second optical probe being a light receiving probe adapted to be connected to a spectrometer and arranged to produce a signal resulting from an interaction of the fluid with said light indicative of the downhole fluid properties;

wherein:

each of said optical probes comprises an elongated body mounted through the wall of the analysis pipe portion in a sealed manner and has a tip, the tip being needle shaped and having an external diameter less than 1 mm; and the first tip of the first optical probe and the second tip of the second optical probe project into a flow section of the analysis pipe portion such that the first tip faces the second tip at a defined distance ranging from 10 µm to 99 mm.

20. The downhole fluid analysis tool of claim 19, wherein the analysis pipe portion comprises a first and a second hole facing each other, a portion of each elongated body being inserted into the analysis pipe portion through the first and second hole respectively, and wherein the device comprises at least one probe connector to couple at least one optical probe in sealed manner to one of the hole, and adapted to adjust the position of said optical probe relatively to the hole of the analysis pipe portion so as to control the defined distance between both tips.

21. The downhole fluid analysis tool of claim 19, wherein the optical probes are directed transversally relatively to a longitudinal axis of the analysis pipe portion.

22. The downhole fluid analysis tool of claim 19, wherein the optical probes are parallel to a longitudinal axis of the analysis pipe portion.

23. The downhole fluid analysis tool of claim 19, wherein the axis of the analysis pipe portion is parallel to an axis of the downhole sampling flow line.

24. The downhole fluid analysis tool of claim 20, wherein the probe connector is chosen among the group comprising a screw nut connection including a conical synthetic rubber/fluoropolymer elastomer ferrule, or a screw nut connection including a metal ferrule, or a screw nut connection including an O-ring, or a welded connection.

25. The downhole fluid analysis tool of claim 20, wherein the analysis pipe portion further comprises a third hole receiving a third optical probe in sealed manner, the third optical probe being positioned perpendicularly relatively to an optical transmission path defined between the first and second optical probe.

26. The downhole fluid analysis tool of claim 19, wherein the optical probe comprises an optical element under the form of an optical fiber and a sapphire tip located in the central portion of the elongated body under the form of a protective tube, an end portion of said optical element forming a tip end adapted to be in contact with the fluid to be analyzed.

27. The downhole fluid analysis tool of claim 26, wherein the optical probe further comprises an electronic board coupled to the optical element and integrating a measurement circuit and a processing module so as to deliver digital measurements on an output cable.

* * * * *